US008153969B2

(12) United States Patent
Fukada et al.

(10) Patent No.: US 8,153,969 B2
(45) Date of Patent: Apr. 10, 2012

(54) INSPECTION METHOD AND INSPECTION SYSTEM USING CHARGED PARTICLE BEAM

(75) Inventors: Atsuko Fukada, Kokubunji (JP); Mitsugu Sato, Hitachinaka (JP); Naomasa Suzuki, Hitachinaka (JP); Hidetoshi Nishiyama, Higashiyamato (JP); Muneyuki Fukuda, Kokubunji (JP); Noritsugu Takahashi, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 194 days.

(21) Appl. No.: 12/323,167

(22) Filed: Nov. 25, 2008

(65) Prior Publication Data
US 2009/0184255 A1 Jul. 23, 2009

Related U.S. Application Data

(63) Continuation of application No. 11/412,976, filed on Apr. 28, 2006, now Pat. No. 7,462,828.

(30) Foreign Application Priority Data

Apr. 28, 2005 (JP) ................. 2005-132528

(51) Int. Cl.
*G01N 23/00* (2006.01)

(52) U.S. Cl. ......... 250/311; 250/306; 250/307; 250/310

(58) Field of Classification Search ............ 250/306, 250/307, 310, 311
See application file for complete search history.

(56) References Cited

U.S. PATENT DOCUMENTS

| 5,502,306 | A | 3/1996 | Meisburger et al. |
| 6,025,593 | A * | 2/2000 | Suzuki et al. ................ 250/310 |
| 6,498,345 | B1 | 12/2002 | Weimer et al. |
| 6,646,261 | B2 * | 11/2003 | Krans ................ 850/1 |
| 6,674,075 | B2 * | 1/2004 | Petrov et al. ................ 250/310 |
| 6,707,041 | B2 | 3/2004 | Essers |
| 6,777,675 | B2 | 8/2004 | Parker et al. |
| 6,787,772 | B2 * | 9/2004 | Ose et al. ................ 850/9 |
| 6,885,001 | B2 * | 4/2005 | Ose et al. ................ 850/9 |

(Continued)

FOREIGN PATENT DOCUMENTS
JP 1-97353 4/1989
(Continued)

OTHER PUBLICATIONS

L. Reimer, "Electron signal and detector strategy in electron beam interactions with solids," 1982, p. 299, SEM Inc.

(Continued)

*Primary Examiner* — Michael Maskell
(74) *Attorney, Agent, or Firm* — McDermott Will & Emery LLP

(57) ABSTRACT

In an electric immersion lens having high resolution capability, secondary electrons generated from a specimen are accelerated to suppress the dependency of rotational action of the secondary electrons applied thereto by an objective lens upon energy levels of the secondary electrons and when selectively detecting low and high angle components of elevation and azimuth as viewed from a secondary electron generation site by means of an annular detector interposed between an electron source and the objective lens, the secondary electrons are adjusted and deflected by means of an E×B deflector such that the center axis of secondary electrons converged finely under acceleration is made to be coincident with the center axis of a low elevation signal detection system and the secondary electrons are deviated from an aperture of a high elevation signal detection system.

7 Claims, 11 Drawing Sheets

U.S. PATENT DOCUMENTS

| | | | |
|---|---|---|---|
| 7,075,078 B2 * | 7/2006 | Ose et al. | 250/311 |
| 7,171,038 B2 | 1/2007 | Adler et al. | |
| 2002/0033449 A1 * | 3/2002 | Nakasuji et al. | 250/306 |
| 2002/0161534 A1 * | 10/2002 | Adler et al. | 702/35 |
| 2003/0062478 A1 | 4/2003 | Frosien et al. | |
| 2003/0219658 A1 * | 11/2003 | Shishido et al. | 430/30 |
| 2005/0098724 A1 * | 5/2005 | Sullivan | 250/310 |
| 2005/0103995 A1 | 5/2005 | Yanagiuchi et al. | |
| 2005/0218325 A1 * | 10/2005 | Nishiyama et al. | 250/311 |
| 2006/0043982 A1 | 3/2006 | Shinada et al. | |
| 2006/0054817 A1 | 3/2006 | Parker | |
| 2006/0060780 A1 * | 3/2006 | Masnaghetti et al. | 250/310 |
| 2006/0186351 A1 | 8/2006 | Nishiyama et al. | |
| 2006/0226360 A1 | 10/2006 | Frosien | |
| 2007/0221846 A1 * | 9/2007 | Todokoro et al. | 250/310 |
| 2007/0230768 A1 * | 10/2007 | Adler et al. | 382/144 |
| 2009/0194690 A1 * | 8/2009 | Nishiyama et al. | 250/307 |

FOREIGN PATENT DOCUMENTS

| | | |
|---|---|---|
| JP | 2-142045 A | 5/1990 |
| JP | 8-273569 A | 10/1996 |
| JP | 10-214586 A | 8/1998 |
| JP | 10-302705 A | 11/1998 |
| JP | 2000-30654 | 1/2000 |
| JP | 2000-188310 A | 7/2000 |
| JP | 2001-141677 | 5/2001 |
| JP | 2001-143649 A | 5/2001 |
| JP | 2002-83563 A | 3/2002 |
| JP | 2003-109532 | 4/2003 |
| JP | 2003-203597 A | 7/2003 |
| JP | 2003-297277 | 10/2003 |
| JP | 2004-047254 | 2/2004 |
| JP | 2004-516461 | 6/2004 |
| JP | 2004-342341 | 12/2004 |
| JP | 2005-100479 A | 4/2005 |

OTHER PUBLICATIONS

Japanese Office Action, w/ partial English translation thereof, issued in Japanese Patent Application No. 2006-122372, dated May 31, 2011.

* cited by examiner (Z-AXIS DIRECTION:FROM SURFACE OF DRAWING SHEET TO DEPTH THEREOF)

INSPECTION METHOD AND INSPECTION SYSTEM USING CHARGED PARTICLE BEAM

RELATED APPLICATIONS

This application is a Continuation of U.S. application No. 11/412,976, filed Apr. 28, 2006, now U.S. Pat. No. 7,462,828, claiming priority of Japanese Application No. 2005-132528, filed Apr. 28, 2005, the entire contents of each of which are hereby incorporated by reference.

BACKGROUND OF THE INVENTION

The present invention relates to a charged particle beam detection system of charged particle beam apparatus and a charged particle beam apparatus equipped with the charged particle beam detection system and more particularly, to a scanning electron microscope (SEM) for forming an image of a signal of electrons such as secondary electrons generated from a specimen while scanning an electron beam. More specifically, the present invention is concerned with method and system for inspecting a substrate having minute circuit patterns such as a semiconductor device or liquid crystal device and particularly, concerned with a review SEM technology of performing pattern inspection and defect review of the semiconductor device and a photo-mask as well.

As generally known, in the SEM for scanning an electron beam on a specimen to form an image of a signal of electrons such as secondary electrons generated from the specimen, the contrast of an acquired image depends on conditions of landing or irradiation of the electron beam on the specimen, for example, irradiation beam current amounts, landing energy levels and potential distribution on the specimen and also, largely depends on the scheme (type) and shape of a detection system. The image contrast is known as including voltage contrast reflecting a charging distribution of the specimen, shadow contrast reflecting topography or unevenness of the specimen surface and substance contrast reflecting differences in the kind of substance of the specimen.

When using the SEM for evaluation/inspection of semiconductor devices, a technology for highly sensitively detecting a delicate uneven portion on the semiconductor device surface to provide a shadow contrast image, among various kinds of image contrast as mentioned above, is thought much of more and more.

A semiconductor device is fabricated by repeating a step of transcribing, through the lithography process and etching process, a pattern formed on a wafer by using a photo-mask. In the fabrication process as above, for the purpose of realizing early start-up of yield and stable running of the fabrication process, it is indispensable to speedily analyze defects found through an in-line wafer inspection and make use of the result of analysis for countermeasures. The key to speedily connecting the result of inspection to the trouble shooting is involved in an automatic defect review/classifying technique for reviewing many detected defects at a high speed and sorting the defects in accordance with causes of generation. As the minuteness of fabrication process advances, the defect size affecting the yield of semiconductor production has also been made to be minute and with an optical type review apparatus, reviewing a defect at high resolution is difficult to achieve. Under the circumstances, a review apparatus of SEM type capable of performing review at high resolution has been put into production. In order to detect a minute foreign matter present on the device and unevenness caused by, for example, scratching as well with this type of apparatus, it is important to obtain a shadow image based on an SEM image equivalent to a shade caused when light is irradiated obliquely. The basic principle of acquisition of the shadow image as above will be described below.

A description will be given by using an example as shown in FIG. 2A in which an uneven portion 101 caused by the presence of a foreign matter in a film is scanned with an electron beam 37 as shown at arrow 41 to irradiate the right side of the uneven portion 101 with the electron beam. Under the irradiation of the electron beam, secondary electrons 38 are emitted. When noticing components of low elevation angles at that time, secondary electrons emitted to the left side are partly shielded by the uneven portion 101. Consequently, the number of secondary electrons detected by a left detector 11 differs from that detected by a right detector 12. Images obtained with the detectors 11 and 12 in this manner provide images emphasized in shadow as shown in FIGS. 2B and 2C, respectively. Therefore, by arranging the detectors on the right and left sides of the primary electron beam 37, the image contrast reflecting the unevenness of the specimen can be obtained.

The principle of obtaining the shadow contrast of the surface by separating secondary electron signals into two directions of right and left is described in, for example, "Electron signal and detector strategy in electron beam interactions with solids" by L. Reimer, published by D. F Kyser et al (SEM Inc., AMF O'Hare IL, P. 299, 1982). In this reference, secondary electrons are not fetched directly by a detector but are caused to impinge upon the bottom surface of an objective lens and electrons generated from the lens bottom surface are separated into tow directions so as to be detected.

Energy distribution of secondary electrons is illustrated graphically in FIG. 3. As well known in the art, secondary electrons are distributed in relation to energy such that the number of components generated at energy levels of about several of eV is the largest, reducing to the number of components at about 50 eV. Also, as shown in the graph, electrons having substantially the same energy as landing energy of the primary electron beam are generated and they are termed so-called reflected electrons or backscattering electrons. The expression of secondary electrons herein implicitly indicates components of backscattering electrons having landing energy approximating that of the primary electron beam. This holds true in the following description.

The technique of acquiring the shadow contrast by separating secondary electrons into right and left components while keeping the outgoing or emitting angle from the specimen of secondary electrons unchanged utilizes the fact that secondary electrons are emitted from a specimen by having a peculiar distribution in the elevation angle direction and a peculiar distribution in the azimuth angle direction in accordance with the unevenness of the specimen and therefore, it is very important for making the shadow highly contrasted that detection is carried out without disturbing the directional distribution of secondary electrons at the time of their emission from the specimen. Conversely, if a process of changing the directional distribution of secondary electrons prevails between the specimen and each of the detectors, the shadow contrast is lowered, failing to discriminate between shadows. Considered as a member affecting the directional distribution of secondary electrons is an objective lens, for instance. As the secondary electrons pass through a magnetic field of the objective lens, the trajectory of secondary electrons undergoes rotational actions in accordance with energy levels of the secondary electrons, so that the directional distribution of the secondary electrons on the specimen is disturbed. Accordingly, for the sake of acquiring the shadow contrast, the right and left detectors are arranged in general under the objective lens, that is, between the specimen and the objective lens as in the aforementioned reference of Reimer.

On the other hand, an SEM especially used in recent years for reviewing defects in semiconductor patterns is generally required to maintain high resolution at a low landing energy level of about 1 keV and to meet this requirement, the construction of components above the specimen, too, is designed optimally. The shorter the distance between the principal plane of a magnetic field of the objective lens and the specimen (called working distance), the higher the resolution can become and therefore, a design is so made as to shorten the distance between the magnetic field center and the specimen. In addition, with the aim of landing the primary beam at a low energy level of about 1 keV while maintaining the high resolution, negative potential (called retarding voltage) is applied to the specimen so that the primary beam may be decelerated for irradiation immediately before the specimen or an objective lens is used in which an electrode at positive potential (called a boosting electrode) effective to permit the beam to be highly accelerated for passage through the objective lens is inserted to thereby superimpose an electromagnetic field and attain the high resolution performance. This kind of lens are also called as electric immersion lens.

As the principal plane of the objective lens approaches the specimen, secondary electrons are involved in the magnetic field of objective lens above the specimen and undergo a rotational action. A known example of achieving the high resolution performance while detecting minute unevenness, backgrounded by the aforementioned principle, is disclosed in JP-A-8-273569, for instance. For attaining the high resolution, an electric immersion lens effective for high resolution is used. Secondary electrons generated from a specimen at low energy levels are rotated by a lens magnetic field through rotation angles according to the energy levels. As a result, after the secondary electrons have passed through the objective lens, their directional information is lost. To cope with this problem, an electric field for accelerating secondary electrons is generated near a wafer to enable the secondary electrons to pass at high speeds through the magnetic field generated by the objective lens, thereby ensuring that the difference in rotation angle dependent on energy can be reduced and the directional information can be preserved. Further, by controlling trajectories of secondary electrons at low energy and backscattering electrons, the backscattering electrons can be detected in an inner annular zone of an annular detector disposed between an electron source and the objective lens and the secondary electrons at low energy can be detected in an outer annular zone. Since the outer annular zone is quartered in the form of sectors to permit selection of azimuth angles of secondary electron emission, acquisition of a shadow image can be assured.

SUMMARY OF THE INVENTION

The acceleration of secondary electrons to high speeds as described above, however, gives rise to a new problem. As compared to secondary electrons not speeded up, highly accelerated secondary electrons are converged relatively finely upon arrival at the detection surface, with the result that, if the center trajectory of secondary electrons is slightly inclined, the balance between right and left angle distributions is disturbed at the time of detection of the secondary electrons by the detectors and a problem of a failure to keep uniform separation arises.

As well known in the art, the optical axis (center axis) of a primary electron beam and that of secondary electrons generally make slight tilt angles to the normal direction of the specimen surface depending on mechanical restriction of parts of apparatus and adjustment conditions in the SEM. In general, the optical axis of the primary electron beam is adjusted such that the influence of inclination is minimized and under such a condition, the SEM is used. On the other hand, it normally suffices that the secondary electrons can be detected merely highly efficiently with the detectors, and the inclination of optical axis of the secondary electrons need not be adjusted. Accordingly, the slightly inclined optical axis of secondary electrons does not matter in many applications. But in the case of, for example, the review SEM in which acceleration of secondary electrons to high speeds, highly contrasted shadow images and highly raised throughput are necessary, the inclination of the optical axis of secondary electrons greatly affects the signal acquisition and eventually the decision of defects.

When the center axis of secondary electrons is inclined, especially, largely, there also occurs a phenomenon that for example, most of secondary electrons are detected with the detector on the one side or a large amount of secondary electrons deviate from a detectable region, failing to be detected. This inconvenience leads to the possibility that in trying to obtain contrast of a very shallow uneven portion, a shadow contrast is so buried in another signal as to disappear. In addition, the apparatus operating as semiconductor reviewer cannot obtain a shadow contrast correctly reflecting a topographic shape, suffering from the possibility that erroneous recognition of defect shapes results.

Further, when only a component of low elevation of secondary electrons is detected as a component reflecting a shadow contrast, separate detection of secondary electrons in the elevation angle direction is needed and in such a case, if the center axis of the secondary electrons shifts from the center axis of the detector, there arises a problem that the elevation angles cannot be separated uniformly irrespective of azimuth angles. And also, the inclination of the optical axis of secondary electrons depends on an adjusted condition of the apparatus and even when the same topographic sample is watched, different contrasts are disadvantageously obtained in accordance with the adjusted condition of the apparatus.

Furthermore, with secondary electrons converged finely, the following problem is raised. More particularly, in case a scan deflector for primary electron beam scan is interposed between the secondary electron detection surface and the specimen, secondary electrons are also converged finely and under this condition, undergoes scanning deflection action. As a result, with the center trajectory of secondary electrons deflected up to an unexpected position on the detection surface, an undetectable region takes place and a non-uniform dark portion is generated in the field of view of a secondary electron image. In this manner, non-uniformity of image quality is caused owing to fine convergence of the secondary electrons.

Moreover, a problem as below is encountered. In a detection system for separating secondary electrons into a plurality of azimuth components about the optical axis of the primary beam, an aperture for passage of the primary beam is needed and the secondary electrons partly pass through the primary beam pass aperture, failing to be detected. As the secondary electrons undergo higher acceleration, components passing through the primary beam pass aperture increase and an increased loss of signal results. Normally, in order for the review SEM and the like to recognize various kinds of defects correctly, not only acquisition of a shadow contrast for recognition of unevenness but also special efficient acquisition of a secondary electron signal going upwards in the normal direction of the specimen surface and not contributing to the shadow is necessary at the same time to obtain a secondary electron image of high S/N. But, with the secondary electrons subjected to high acceleration, most of them pass through the beam pass aperture unless otherwise treated and detection of a normal direction component becomes impossible.

The non-uniformity in the field of view of detection signal attributable to deflection and aperture of the detection system also depends on the kind of specimen. As known in the art, when the specimen is irradiated with the electron beam, having its surface charged, the trajectory of secondary electrons change to aggravate the non-uniformity in the field of view of an acquired image in some applications.

To cope with the situation that secondary electrons pass through the aperture of the detection system toward the electron gun, thus failing to be detected, a technique is known which deviates the secondary electrons from the optical axis to assure efficient detection of them. As an example, JP-A-10-214586 or U.S. Pat. No. 6,674, 075 Specification is known. Either reference discloses a technique according to which not only the optical axis of secondary electrons but also the optical axis of a primary electron beam is deflected by means of a deflector so that the secondary electrons may be deviated from their originally expected trajectory to permit a signal to be acquired with a detector disposed to be out of the optical axis. Disadvantageously, this expedient cannot be used as it is because aberration is caused by the deflection of the primary beam and the resolution is degraded in the SEM required of high resolution as described previously. Even if the aberration is permissible, the scale of the apparatus is disadvantageously increased by the separation of the optical axes through deflection of both the primary beam and secondary electrons.

A technique for deflecting secondary electrons to the outside of the optical axis while maintaining high resolution is known as described in JP-A-02-142045. The known reference discloses an electric immersion deflector (termed a so-called Wien filter or E×B deflector) in which for orthogonally superimposing an electric field on a magnetic field so as not to apply deflection action on the primary beam but to apply deflection action only on secondary electrons. Hereinafter, this kind of electromagnetic deflector is referred to as an E×B deflector. In the E×B deflector, the primary beam does not undergo the deflection action in essentiality and therefore, as compared to the case of deflection by an ordinal deflector, aberration of the primary beam can be reduced drastically. Electrons confined in the beam have a width of energy and strictly speaking, a slight difference takes place between deflection angles by the electromagnetic field, causing chromatic aberration leading to a slight reduction in resolution. In the known reference, however, two E×B deflectors are mounted, thereby ensuring that chromatic aberration caused when the primary beam passes through the one E×B deflectors can be canceled by the other E×B deflector so as to decrease the aberration. The secondary electron detector is interposed between the two E x B deflectors, so that secondary electrons deflected by the lower stage of E×B deflector can be detected. But, the known reference does not disclose compatibility with the construction of the detection system capable of obtaining a shadow image as described previously.

Known examples of the use of one E×B deflector are described in JP-A-2001-143649, JP-A-2003-203597 and JP-A-2000-188310. According to a disclosed technology, a detection system using one stage of E×B deflector and a reflecting plate as well is provided in order that the secondary electron beam can be deflected so as to get clear of the optical axis but can impinge upon the reflecting plate to newly generate signal electrons which in turn are detected and consequently, highly efficient detection can be assured even with a small deflection angle. Even the known references, however, also fail to disclose the compatibility with the construction of the detection system capable of obtaining shadow images as described previously.

Further, in connection with the E×B deflector, a technology for superimposition of a decelerating electric field on the E×B deflector is disclosed in JP-A-10-302705 or JP-A-2005-100479. According to the technology in these references, the resulting device is operated as an energy filter for performing disclaminate at a specified energy level of secondary electrons to improve energy discrimination accuracy. Furthermore, JP-A-2002-083563 discloses a technique for switching between the high resolution mode and the shadow image acquisition mode. But, this reference does not disclose the technique for acquiring shadow images with high accuracy while maintaining the high resolution performance and acquiring secondary electron images with high efficiency, either.

Because of the above problems, the prior arts have difficulties in performing constantly stable detection of shallow unevenness with secondary electrons accelerated while maintaining high resolution. And also, the accuracy of separate detection of secondary electrons based on elevation angles in the outgoing or emitting direction is lowered by the shift between the center axis of the detection system and that of secondary electrons. Further, it is difficult to obtain a uniform secondary electron image within the field of view and obtain a normal component of secondary electrons going upward from the specimen surface in the normal direction with high efficiency so as to acquire a secondary electron image of high S/N ratio while maintaining high resolution with highly accelerated secondary electrons and acquiring shadow images.

A first object of the present invention is to prevent degradation in shadow contrast due to inclination of the center axis of secondary electrons and to perform constantly stable detection of shallow unevenness even when the secondary electrons are accelerated to high speeds by an electromagnetic field efficient to obtain high resolution. A second object of the invention is to prevent degradation in elevation angle separation accuracy attributable to a shift between the center axis of a separation detector and the center axis of secondary electrons in course of detection of secondary electrons in which secondary electrons are separated in accordance with elevation angles in the outgoing or emitting direction. Further, a third object of the invention is to reduce the non-uniformity in the field of view and loss of secondary electron signal attributable to fine convergence of secondary electrons.

According to the present invention, to accomplish the first and second objects, a deflector for secondary electrons is arranged which is adapted to adjust only the optical axis of secondary electrons independently of a primary beam under the condition that an electric immersion lens is used as an objective lens with the aim of attaining high resolution, that is, accelerating secondary electrons, whereby the center axis of secondary electrons is made to be coincident with the center axis of separation of a separation detector and the secondary electrons are detected uniformly separately. To accomplish the third object, the deflector for secondary electrons is operated such that secondary electrons undergoing high acceleration can be detected without loss. To meet the objects as above, in an embodiment, the deflector for secondary electrons is so constructed as to have ability to deflect secondary electrons in at least two directions which are orthogonal to each other. The secondary electron detection system is also constructed so as to reduce the loss in compliance with the deflection of secondary electrons.

According to the present invention, in inspection of a partially completed substrate of a semiconductor device having circuit patterns, shallow unevenness and minute foreign matters can be detected with high sensitivity while maintaining high resolution and can be reviewed and classified. Thus, semiconductor products can be monitored with high sensitivity to make it easy to specify or identify causes of defects.

Other objects, features and advantages of the invention will become apparent from the following description of the embodiments of the invention taken in conjunction with the accompanying drawings.

DESCRIPTION OF THE INVENTION

Figure 4:
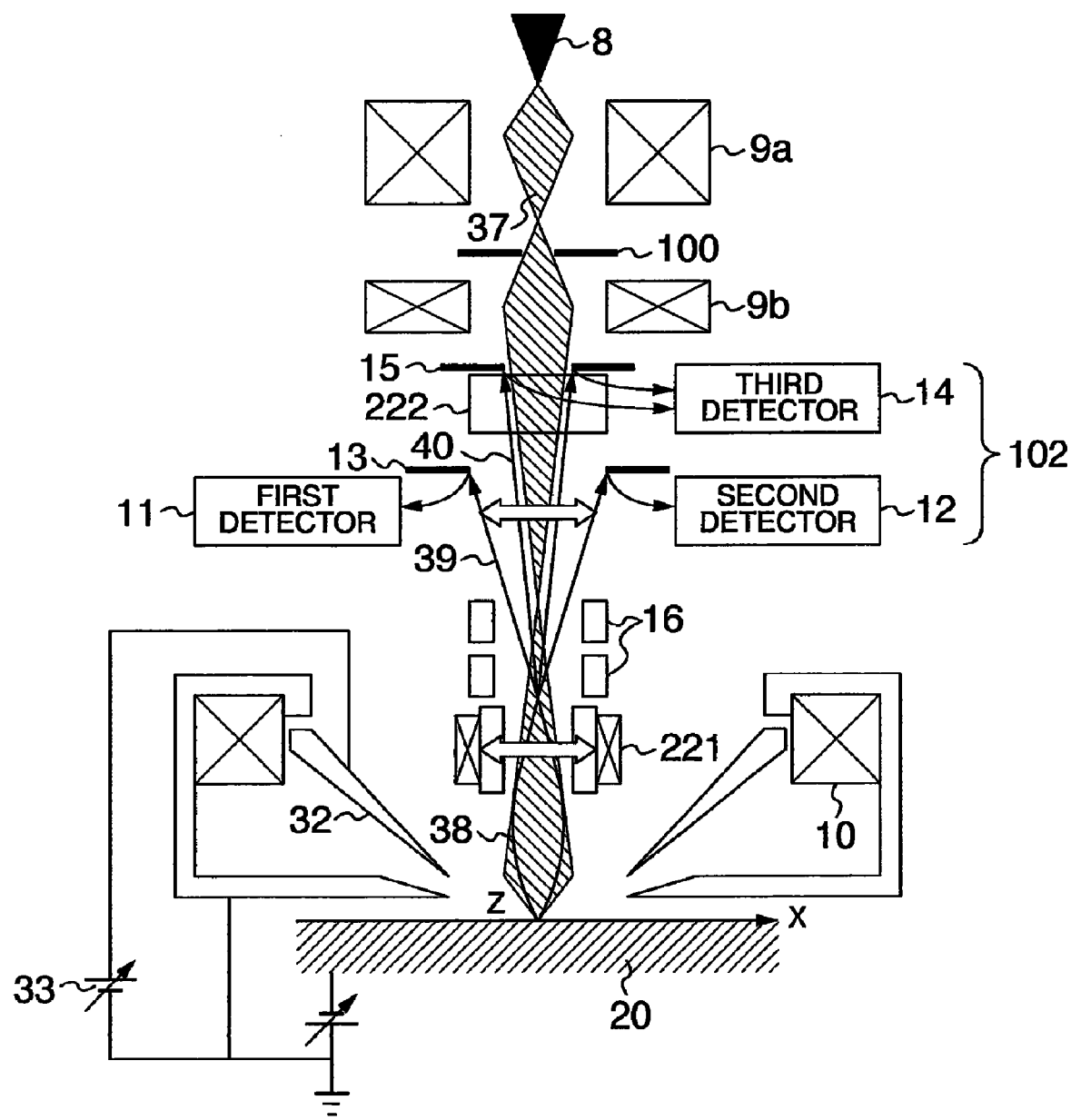
FIG. 4 is a schematic diagram showing the principal part of an example of an electron optics to which the invention is applied.

Referring first to FIG. 4, an electron optics to which the present invention is applied has the principal part as exemplified therein in schematic diagram form. The electron optics is an apparatus comprising an electron source 8, an objective lens 10, a specimen (semiconductor wafer) 20, an accelerating electrode 32 opposing the specimen, a deflector for secondary electrons (E×B deflector) 221, a scan deflector for primary electron beam 16 and a detection system 102 interposed between the electron source and the objective lens 10. The deflection system 102 includes upper and lower reflecting plates 13 and 15 and detectors 11,12 and 14. As described previously, the E×B deflector 221 is a deflector for superimposition of an electric field on a magnetic field, which deflector is set such that amounts of deflections acting on a primary electron beam by the electric field and magnetic field, respectively, are mutually equal in inverse directions so as to cancel the deflection actions mutually and amounts of deflections acting on secondary electrons by the electric field and magnetic field, respectively, are in the same direction, thereby making it possible to deflect only the secondary electrons independently.

Figure 3:
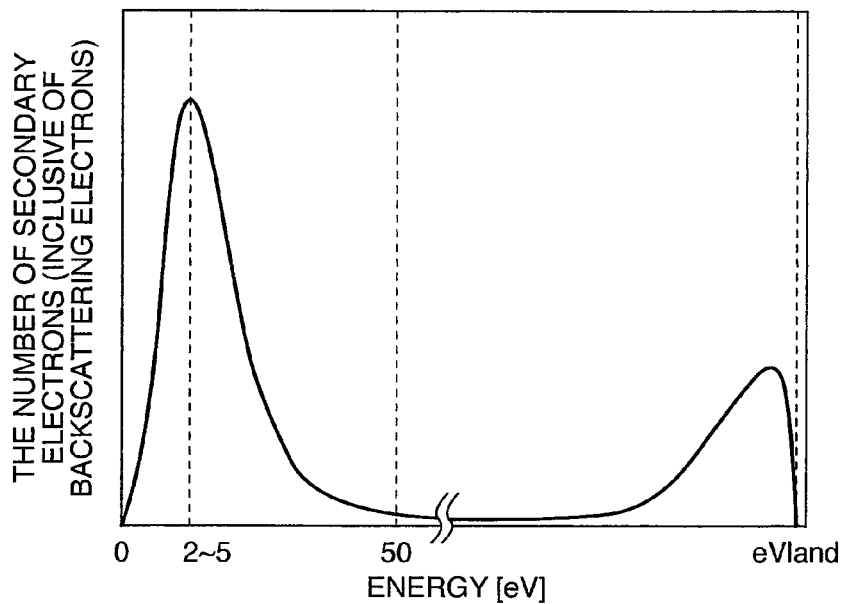
FIG. 3 is a graph showing energy distribution of secondary electrons.

In this type of apparatus, secondary electrons 38 generated under irradiation of an electron beam 37 emitted from the electron source 8 on the wafer 20 have an energy distribution as shown in FIG. 3. The secondary electrons 38 ascend while being rotated by a magnetic field generated by the objective lens 10. At that time, if the secondary electrons 38 pass through the magnetic field at low speeds, the rotation angle of secondary electrons 38 depends on the energy of secondary electrons 38 and directional information cannot be preserved. Then, in order to relatively suppress the dependency of the rotation angle of secondary electron on the energy, a sufficiently high level of positive potential, for example, about several of kV relative to the wafer is applied to the accelerating electrode 32 opposing the wafer, thus permitting the secondary electrons 38 to pass through the magnetic field at high speeds. As a result, the secondary electrons originally having an energy level of about several of 10 eV at the most are accelerated by the potential difference of about several of kV and therefore, the difference in rotational action due to the energy difference of several of 10 eV in course of passage through the objective lens hardly appear in the result. In other words, the secondary electrons are detected by the detection system 102, with the directional distribution on the specimen surface maintained substantially, and the directional information can be preserved.

Through the use of the directional information, secondary electrons 40 at large elevation angles and secondary electrons 39 at small elevation angles are caused to impinge upon the upper and lower stages of two reflecting plates 15 and 13 and then, electrons generated from the reflecting plates are detected to permit signal separation in accordance with elevation angles. For example, a low angle component of small elevation angle is detected by the lower stage of reflecting plate and a detector. When the lower stage of reflecting plate is constructed of, for example, two sections separated in azimuth directions, separate detection of signals of low elevation angle components in right and left directions can be assured to provide a shadow-like contrast obtained by obliquely lighting an uneven portion.

At that time, the deflector for secondary electrons (E×B deflector) 221 is operated to finely adjust the optical axis of secondary electrons on the xz plane in FIG. 4 independently of the primary beam. Without operating the E×B deflector, the optical axis of secondary electrons shifts by a slight angle θ and hence, does not coincide with the center axis of the detection system on the detection plane to lower the accuracy of separation in the azimuth direction but with the E×B deflector operated, the center axis of the detection system coincides with the optical axis of secondary electrons and directional information generated on the specimen surface can be reflected correctly on a separate detection signal.

The secondary electron alignment operation as above is carried out in the xz direction on the sheet of drawing but it can also be done in yz direction as necessary, so that the signal can be deflected in a desired direction to improve the accuracy of shadow contrast of specimen unevenness, reduce the loss of the signal and reduce the non-uniformity of the image.

It will be appreciated that when the reflecting plate is constructed of a multi-channel plate or a scintillator, secondary electrons generated from the wafer can be detected directly to attain similar effects.

The present invention will be described more specifically by using embodiments thereof.

Embodiment 1

In the present embodiment, an instance will be described in which defect classifying is done by using a review SEM.

Figure 1:
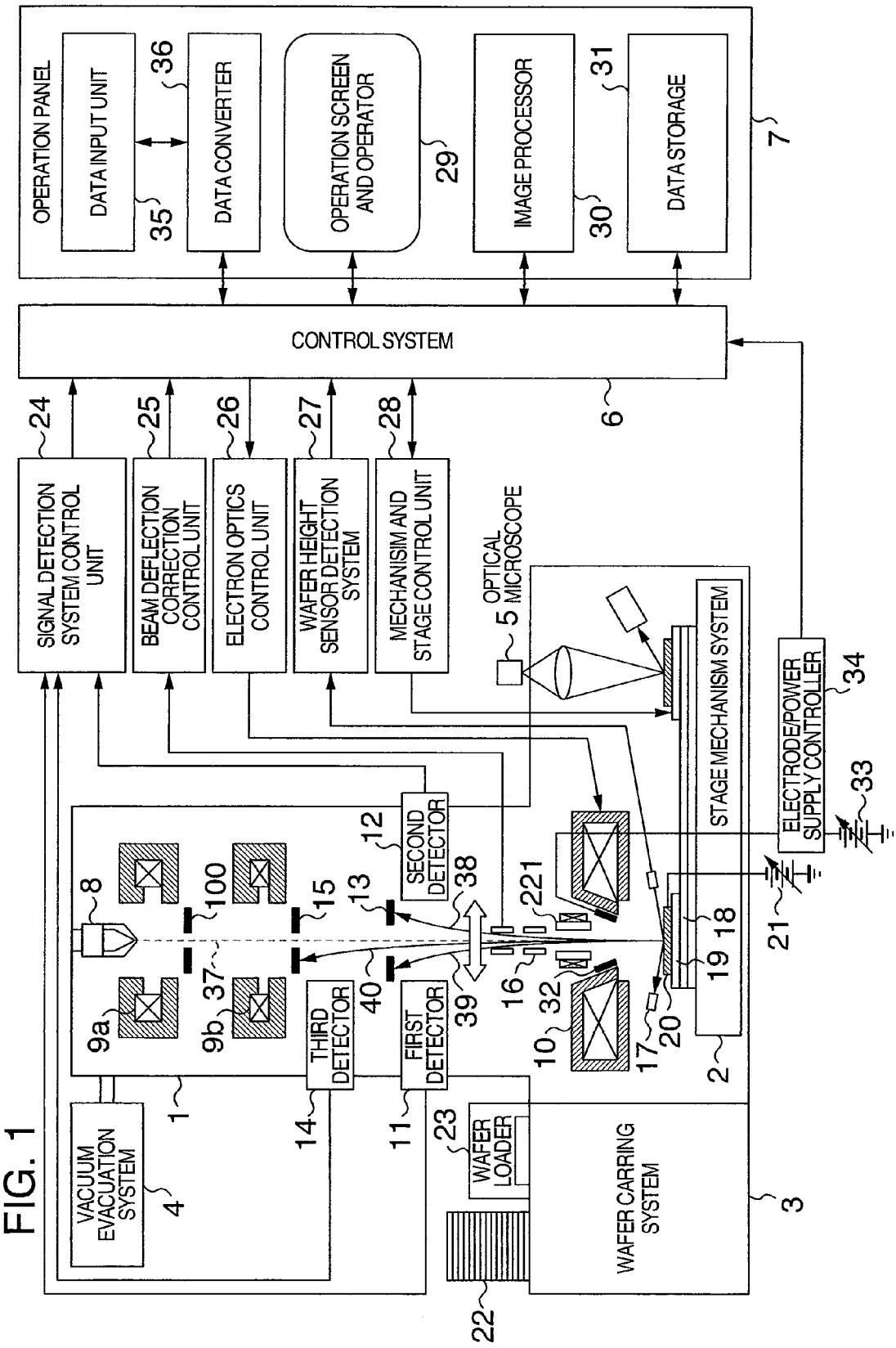
FIG. 1 is a diagram showing an example of construction of a review SEM.
Figure 2A:
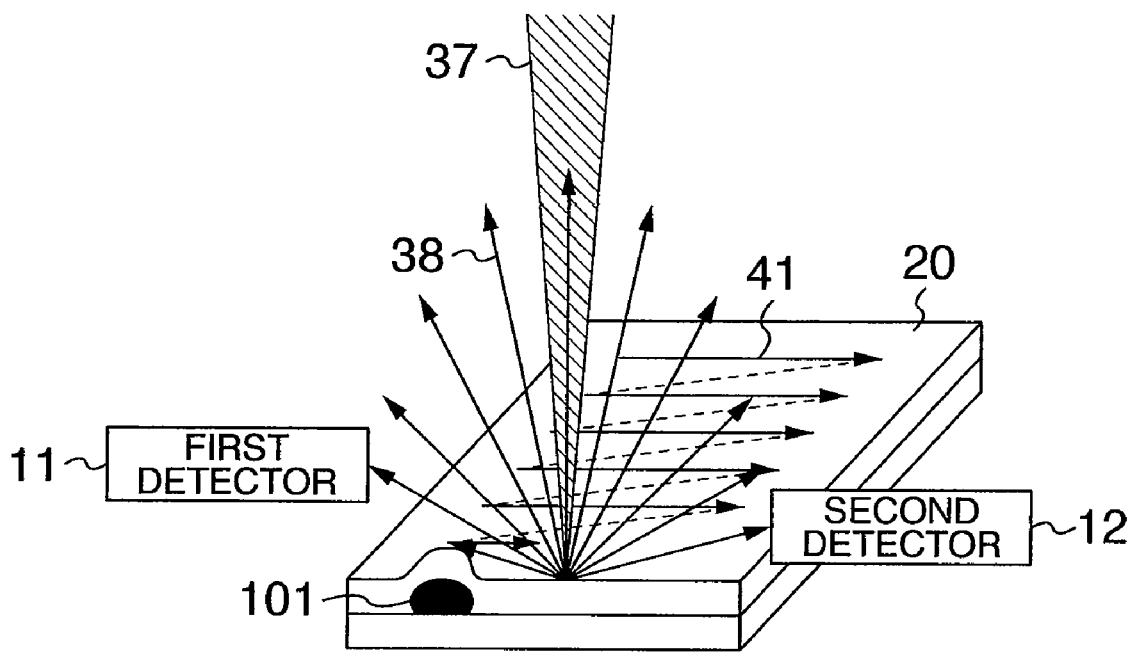
FIGS. 2A to 2C are diagrams useful to explain the principle of formation of shadow images by an SEM.
Figure 2B:
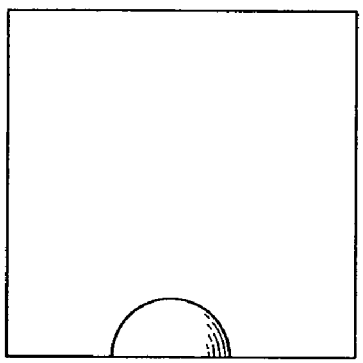
Figure 2C:
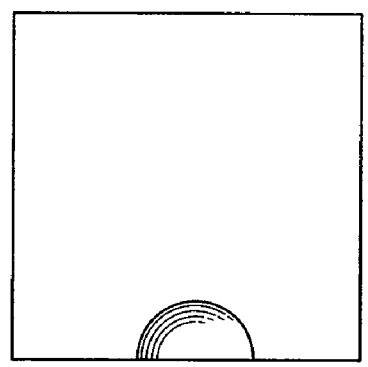

The review SEM is constructed as exemplified in FIG. 1. The present apparatus comprises an electron optics 1, a stage mechanism system 2, a wafer carrying system 3, a vacuum evacuation system 4, an optical microscope 5, a control system 6 and an operation panel 7.

The electron optics 1 includes an electron source 8, a condenser lens 9, an aperture 100, an objective lens 10, a first detector 11, a second detector 12, a first reflecting plate 13, a third detector 14, a second reflecting plate 15, a scan deflector 16, a wafer height sensor 17, an accelerating electrode 32 arranged to oppose the stage, an electrode power supply 33, an electrode power supply controller 34 and a deflector for secondary electrons (E×B deflector) 221. The construction and operation of the principal part of electron optics have already been explained with reference to FIG. 4.

The stage mechanism system 2 includes an XY stage 18, a holder 19 for mounting a specimen in the form of a wafer and a retarding power supply 21 for applying negative voltage to the holder 19 and wafer 20. The XY stage 18 is attached with a position sensor based on laser measurement.

The wafer carrying system 3 includes a cassette mount 22 and a wafer loader 23. The holder 19 mounted with the wafer 20 is caused to reciprocate between the wafer loader 23 and XY stage 18.

The control system 6 includes a signal detection system control unit 24, a beam deflection correction control unit 25, an electron optics control unit 26, a wafer height sensor system 27 and a mechanism and stage control unit 28. The operation panel 7 includes an operation screen and operator 29, an image processor 30 and an image/inspection data storage 31.

Next, operation of the individual components in FIG. 1 will be described. Firstly, a wafer cassette having at its arbitrary shelf a wafer 20 set is placed on the cassette mount 22 in the wafer carrying system 3. Subsequently, for the sake of designating the wafer 20 to be reviewed, a shelf number in cassette at which the wafer 20 is set is designated from the operation screen 29. In review operation, observation through an electron beam image is executed on the basis of inspection result information including position information of defects obtained through an inspection executed by a different inspection apparatus and therefore, an inspection result file is selected by means of the operation screen and operator 29. In selection, it is possible to read the inspection result file through communication based on, for example, network or to read the inspection result file from a medium such as floppy disk. In any case, by designating an inspection result file name, various kinds of data of the inspection result can be read to a data input unit 35 and can be converted by a data converter 36 into data format and coordinates for use by the review SEM. Further, a review condition file name is inputted by means of the operation screen and operator 29. The review condition file is formed by combining various parameters for determination of the contents of review. Inputting a condition necessary to execute the review is completed and the sequence of automatic review is started.

With the review started, the set wafer 20 is first carried to the interior of the review apparatus. In the wafer carrying system 3, any case where the diameters of wafers to be inspected differ and/or wafers are shaped differently to have the orientation flat type or the notch type can be attended to by exchanging the holder 19 mounting the wafer 20 so as to meet the size and shape of wafer. The wafer to be inspected is taken out of the cassette, fixedly mounted on the holder 19 by means of the wafer loader 23 including an arm and a preliminary vacuum chamber and conveyed, along with the holder, to an inspection chamber.

After the wafer 20 has been loaded, the electron optics control unit 26 sets electron beam landing conditions to the individual components on the basis of the inputted review condition. Then, an electron beam image at a predetermined site on wafer 20 is acquired and a focus/astigmatism adjustment is made on the basis of the image. At the same time, the height of wafer 20 is determined by the wafer height sensor 17 and the correlation between the height information and an in-focus condition of electron beam is determined, thereby ensuring that during subsequent acquisition of electron beam images, the in-focus condition can automatically be adjusted in accordance with the result of wafer height sensor without executing the in-focus adjustment for each operation of electron beam image acquisition. This permits high-speed consecutive electron beam image acquisition.

After the setting of electron beam landing condition and the adjustment of focus/astigmatism have been completed, alignment is carried out using two points on the wafer.

Rotation and coordinate values are corrected on the basis of the result of alignment and movement to a position of a defect to be reviewed is effected on the basis of various kinds of information in the inspection result file which has already been read.

Figure 5:
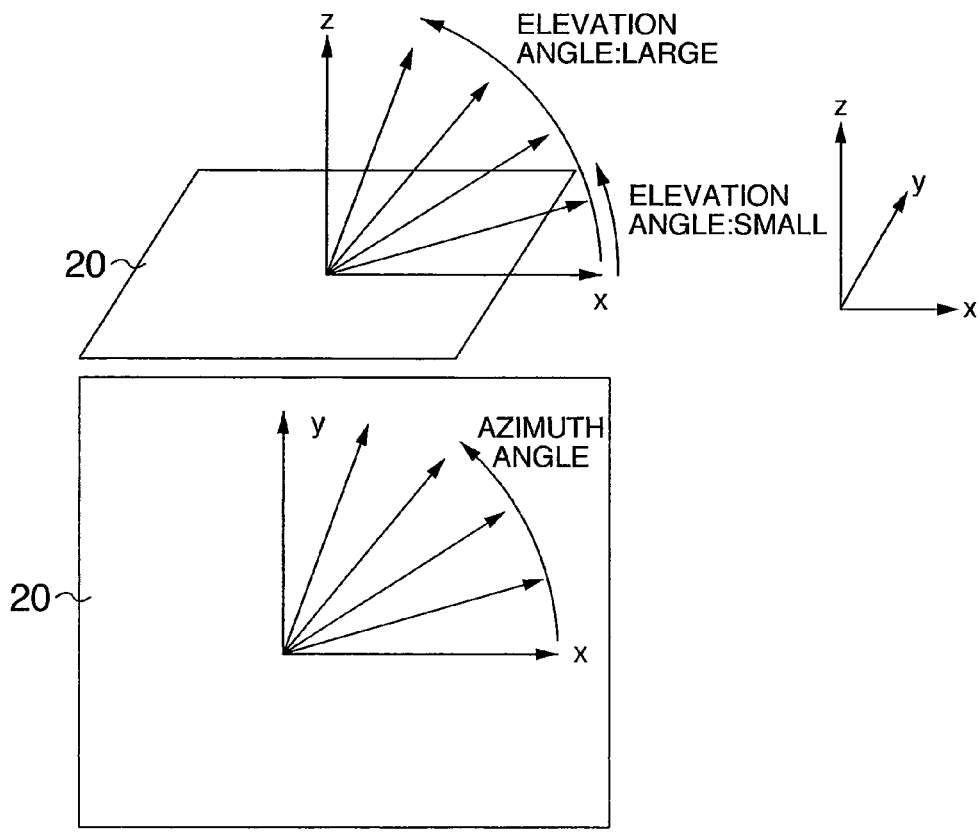
FIG. 5 is a diagram useful to give the definition of outgoing or emitting angles of secondary electrons.

With the movement to the defect position completed, beam irradiation is conducted. Each of the reflecting plates 13 and 15 is of a plate structure formed with a primary beam pass aperture so that, in accordance with the emission elevation angles of secondary electrons, a low angle component may be caused to impinge on the reflecting plate 13 and a high angle component may be caused to pass through the aperture in the reflecting plate 13 and thereafter to impinge on the reflecting plate 15. As shown in FIG. 5, of the emission directions of secondary electrons, "elevation" defines a direction which makes 0° to 90° from the specimen surface to the perpendicular and "azimuth" defines a radial direction set by a rotary angle about the normal on the specimen. Secondary electrons having low angles in the elevation direction are separated to the right or the left depending on azimuth angles so as to impinge on the reflecting plate 13. As a result of impingement of secondary electrons on the reflecting plate, secondary electrons are newly generated from the reflecting plate, so that secondary electrons generated near the detector 11 are directed thereto and secondary electrons generated near the detector 12 are directed thereto. Meanwhile, secondary elections impinging on the reflecting plate 15 are responsible for generation of secondary electrons therefrom which are detected by the detector 14. By applying each of the detectors 11, 12 and 14 with potential for attracting electrons thereto, the detection efficiency can be improved. Although not illustrated, a mesh electrode or an E×B deflector can be arranged near the reflecting plate 13, 15 to form an electric field/magnetic field distribution for attracting generated electrons toward the closest detector as viewed from electrons impinging upon the reflecting plate. Especially, an E×B deflector not shown can be arranged in the vicinity of the reflecting plate 15 to attract secondary electrons generated from the reflecting plate 15 to the detector 14 without having the influence of aberration upon the primary beam, thereby improving the detection efficiency. Furthermore, to prevent mixing of L and R signals, a partition plate may be arranged between the left-side and right-side sections of reflecting plate. In this manner, shadow images intensified in contrast can be obtained at the detectors 11 and 12 and a substance image can be obtained at the detector 14. To add, in the present embodiment, the reflecting plates are used so that signal electrons from the specimen may once be caused to impinge on the reflecting plates and newly generated secondary electrons may be detected but obviously, without resort to the reflecting plate, a detector of axially symmetrical shape may be arranged to directly detect signal electrons from the specimen. In this case the detector may be constructed of a scintillator and prism, a light guide and a photo-multiplier to derive a detection signal but otherwise, signal extraction may be effected with a curved light guide.

As described above, the shadow contrast emphasizing image signal is principally obtained with the detectors 11 and 12 and the substance contrast signal is principally obtained with the detector 14. Therefore, in the signal detection system control unit 24, the circuit construction is such that as necessary, signals of the detectors 11, 12 and 14 can be extracted independently of one another or signals of detectors 11, 12 and 14 which have undergone operation processes, for example, the sum of the signals of detectors 11, 12 and 14 or the difference signal between the signals of detectors 11 and 12 can be extracted.

The reflecting plate 15 has the beam pass aperture in the center to permit passage of the primary beam from above to below and because of the necessity of decreasing, as far as possible, the loss of signal due to passage of secondary electrons from below to above, the beam pass aperture is formed having a radius of 0.5 mm.

Figure 7:
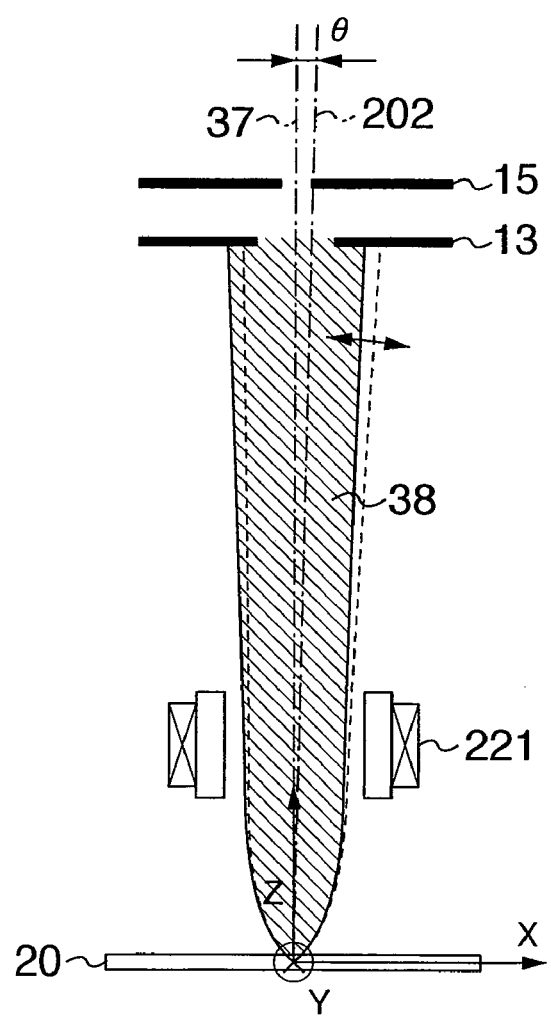
FIG. 7 is a diagram showing the model of operation of secondary electron deflection.

At the time of image acquisition, alignment of secondary electrons can be performed by operating the E×B deflector 221. The alignment of secondary electrons will be described with reference to FIG. 7. The E×B deflector 221 is operated to deflect the center trajectory 202 of secondary electrons by an angle of θ. Through this, balancing of directional components during impingement of secondary electrons 38 on the lower reflecting plate 13 is changed.

The background the present embodiment needs will be described. In the electro-optic apparatus as in the present invention, it is general that the optical axis of a primary electron beam and that of secondary electrons are inclined relative to the normal direction of the specimen surface by a slight angle in accordance with mechanical restrictions and adjustment conditions of the apparatus. In general, for the primary electron beam, its optical axis is so adjusted as to permit the inclination to have the minimal influence upon the use. Meanwhile, normally, highly efficient detection is simply required of secondary electrons and there is no need of adjusting the inclination of optical axis of secondary electrons.

In the configuration of the present invention, however, the detection system for separation of secondary electrons into two or more elevation directional components is provided and with the center trajectory of secondary electrons inclined relative to the center of the aperture in the reflecting plate, the directional accuracy of separation of secondary electrons is degraded. Further, in case the center axis of secondary electrons is inclined largely, there occurs a phenomenon that, for example, most of secondary electrons are detected by the detector on the one side or a large amount of secondary electrons deviate from the detectable region, failing to be detected. This problem gives rise to the possibility that in making an attempt to obtain contrast of a very shallow unevenness, shadow contrast is so buried in another signal as to disappear. In the apparatus of reviewing semiconductors, the topographic shape cannot be acquired in the form of a correct shadow contrast and possibly, a defect shape is recognized erroneously.

To cope with these problems, in the present embodiment, the optical axis of secondary electrons is deflected independently of the optical axis of primary electron beam 37 to adjust balancing of directional components upon impingement on the reflecting plate 13 to a desired direction.

This will be described more specifically. When secondary electrons are separated at the reflecting plate 13 in the right and left directions under the condition that the center trajectory 202 of secondary electrons passes through the center of the aperture in the reflecting plate 13, secondary electrons generated from the horizontal surface of the specimen are uniformly separated in the right and left directions and signal amounts SR and SL obtained at the right and left detectors are related to each other by SR=SL. On the other hand, with the center trajectory 202 of secondary electrons non-coincident with the center of the aperture in reflecting plate, signals from the horizontal surface are not separated uniformly in the right and left directions and SR≠SL stands. For the purpose of accurately separating signals reflective of a shadow of an uneven portion per se on the specimen as in the case of the present invention, it is first important to assure uniform separation of signals from the horizontal surface of the specimen in the right and left directions.

Figure 8A:
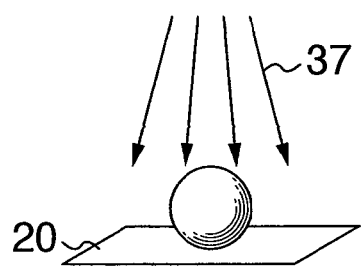
FIGS. 8A and 8B are diagrams for explaining a method of adjusting the secondary electron deflection.
Figure 8B:
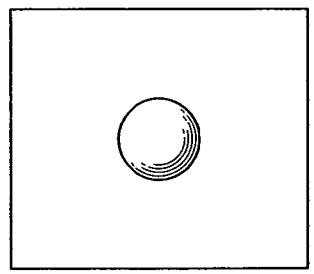

Then, as shown in FIG. 8A, for example, an electron beam 37 is irradiated on a spherical sample while being scanned and the deflection angle θ by the E×B deflector 221 is adjusted such that just the half of the sphere is shadowed in an obtained image as shown in FIG. 8B. In the adjustment by the E×B deflector 221, for keeping the primary beam from undergoing deflection action, the electric and magnetic fields having intensities balanced must be applied to cancel the deflection action on the primary beam. To this end, operation is carried out under a precedently stored operational condition that the electric and magnetic fields can be applied by keeping balance between their intensities or adjustment is made while watching an image such that the image is not moved from a site set at the time of non-operation of the E×B deflector. In this manner, the optical axis angle of secondary electrons is adjusted by changing the deflection amount while keeping the balance between electric and magnetic field intensities. In adjustment, the adjustment accuracy can be improved by making an adjustment such that the shadow contrast of the spherical surface or inclined surface can be uniform in the right and left while watching the spherical sample as described above or a sample of known unevenness. The right and left signal amounts SR and SL are so adjusted as to be uniform through the adjustment as above and hence, by acquiring a shadow image of an unknown sample representing an observation object, the shadow of an uneven portion of the specimen as it is can be imaged in the form of a shadow contrast with high accuracy.

In the electron optics in which secondary electrons generated from the specimen are accelerated by the electric field above the specimen, spreading or divergence of secondary electrons is relatively reduced and therefore the balance between right and left amounts of secondary electron signals is disturbed largely by a slight inclination of the axis of secondary electrons. For this reason, the aforementioned adjustment is essentially indispensable for accurate acquisition of shadow images in this type of electron optics.

And also, the E×B deflector 221 can be arranged anywhere on the optical axis below the reflecting plate 13. But, the larger the distance of lower position from the reflecting plate 13, the larger the deflection amount obtained with a small deflection angle θ becomes, that is, the wider the adjustment range becomes, thereby concurrently ensuring that the E×B deflector can have less influence of resolution degradation upon the primary electron beam.

Figure 6A:
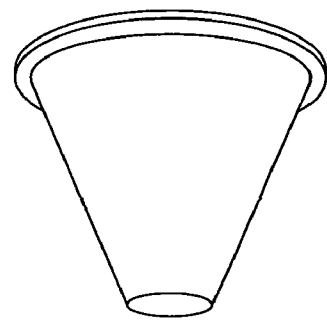
FIGS. 6A and 6B are diagrams showing examples of the shape of a reflecting plate.
Figure 6B:
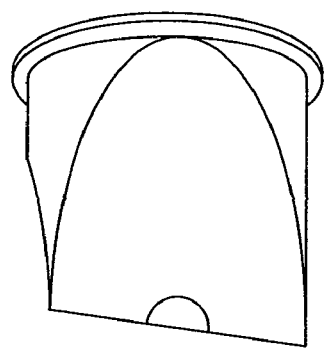

It will be appreciated that the shape of the reflecting plate need not always be planar but it may make use of a slant as shown in FIG. 6A or 6B. To add, a multi-channel plate, a semiconductor detector or a scintillator may substitute for the reflecting plate 13 or 15 to provide a detection system for direct acquisition of signals.

The thus acquired image may be preserved in the image/ data storage 31 as necessary. Either precedent storage or non-storage may be set in the review condition file or as necessary, a plurality of kinds of images obtained from a plurality of detectors may be stored concurrently in accordance with setting.

Concurrently with storage of the image, the image processor 30 extracts features of a defect from the image information and automatically classifies the contents of the defect. Since a shadow image reflecting the unevenness of the specimen can be obtained, the use of the shadow image makes it possible to easily and accurately decide whether the defect portion of the specimen is an uneven defect and further, whether it is concave or convex and to visualize (review) the state of the defect more clearly. By using the unevenness information of the specimen defect portion, more accurate and effective automatic classification of the defect can be assured. For performing the review and automatic classification at higher throughput, it is necessary that with beam irradiation or landing within as short a time as possible, the secondary electron signal be separated and detected efficiently and accurately by means of the individual detectors to make an accurate decision of unevenness of a minute defect. In this respect, it has been proven that the technique for alignment of secondary electron signal according to the invention can improve the accuracy of the result of detection drastically. The results of classifying are encoded to numerical values of, for example, 0 to 255 and a code number is written to a data field corresponding to a defect classifying code in the inspection result file.

When in one sheet of wafer a series of operations as described previously are completed for all defects designated as objects subject to review execution, an inspection result file (written with the results of classification) is automatically preserved and is then delivered to a designated destination. Thereafter, the wafer is unloaded to end the review.

By using the present method, uniform separation of low and high angle components in terms of secondary electron emitting elevation angles can be assured independently of azimuth angles and in addition, highly accurate discriminative detection of signals in the azimuth directions can be permitted, so that a defect detected through, for example, optical inspection can be detected with high sensitivity and reviewed and classified.

In the present embodiment, the deflector 16 for scan deflection of the primary electron beam is constructed in two-stage form to set up the deflection center of the scan deflection in the lens center of the objective lens. The scan deflector 16 can be of either a magnetic type deflector or an electrostatic type deflector. With a view to further reducing the deflection area on the surface of detection of secondary electrons, the electrostatic type scan deflector is efficient.

Embodiment 2

Next, a second embodiment will be described. The overall construction is similar to that of the first embodiment shown in FIGS. 1 and 4. Structurally, in the second embodiment, an E×B deflector 221 is constructed of a quaternary electrode and a quaternary magnetic pole in order that secondary electrons can be deflected at all azimuth angles. Accordingly, alignment of secondary electrons can be accomplished in not only the separation direction of reflecting plate 13 (x direction in the figure) but also a direction vertical to the sheet of drawing (y direction). Through this, the center axis direction of secondary electrons can be corrected for shift in y direction in relation to the aperture formed in the reflecting plate 13. In addition, secondary electrons can be so adjusted as to impinge upon the reflecting plate 15 at a desired part. As will be seen from the above, with the optical axis of secondary electrons aligned in both the x and y directions, signals can be obtained by causing secondary electrons emitted from the sample surface at the same elevation angle to impinge upon the reflecting plate 15 or 13 uniformly irrespective of the azimuth angle.

Embodiment 3

Figure 9:
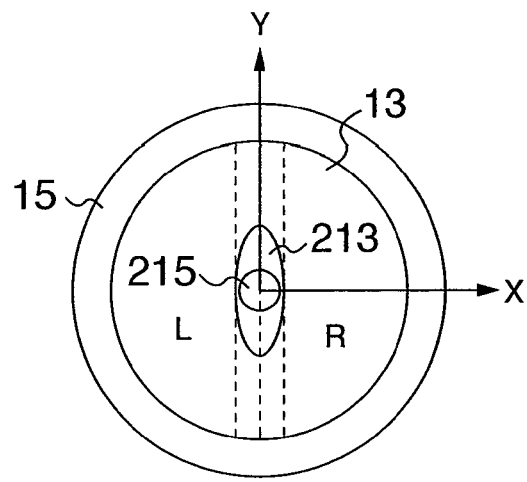
FIG. 9 is a bottom view of a reflecting plate shape according to a third embodiment.

Next, a third embodiment will be described. Structurally, the present embodiment is identical to the second embodiment with the only exception that reflecting plates 13 and 15 are constructed as shown in FIG. 9 when viewed from the specimen. More particularly, where the direction of secondary electron separation by the reflecting plate 13 is in x direction, a direction vertical to the x direction is y direction and the optical axis of the primary electron beam is in z direction, a beam pass aperture 213 in the reflecting plate 13 has an ellipsoidal shape having a major axis in y direction and a minor axis in x direction and a beam pass aperture 215 in the reflecting plate 15 has a circular shape having a diameter smaller than the major axis of the aperture 213. Needless to say, a pass aperture 213 having a rectangular shape or the like can attain the same effect and can be included in the present invention. For operation, this structure is used in combination with the quaternary pole E×B deflector of the second embodiment.

With this construction, the secondary electron alignment for improving the separation accuracy when separating right and left signals in x direction as in the case of the first embodiment can be assured on the one hand and the deflection of secondary electrons in y direction at the reflecting plate 15, on the other hand, can be assured in such a way that the secondary electrons do not pass upwardly through the pass aperture 215 but impinge upon the reflecting plate 15. Through this secondary electron deflection, the adjustment can be made in such a way that the right and left separation accuracy can be improved without degrading the resolution of the primary beam and electrons having passed through the reflecting plate 13 can be prevented from going upwards and being lost, thus succeeding in impinging upon the reflecting plate 15, with the result that an electron signal image free from signal loss at the detector 14 can be acquired.

The third embodiment has the following advantages. When secondary electrons 38 are detected above the scan deflector 16 as in the present embodiment, the secondary electrons 38 also pass through the scan deflection electric field or magnetic field and are then deflected. Especially when the secondary electrons 38 are converged finely at the height of the reflecting plate 15, the emitting position from the specimen and the scan deflection signal are responsible for coexistence, in the same field of view, of a case where most of the secondary electrons go upwards through the beam pass aperture 215 in reflecting plate 15 and an image signal can hardly be obtained and a case where most of the secondary electrons do not go upwards but impinge on the reflecting plate 15 and an image signal can be obtained, thus forming a dark portion caused by the aperture in an image. But, according to the present embodiment, secondary electrons 38 can be deflected in the y direction so as not to go upwards through the beam pass aperture 215 and as a result, a uniform image devoid of a shadow of the pass aperture can be obtained. And besides, since the ExB deflector for secondary electron 221 does not apply the deflection action on the primary beam, this advantage can be obtained by satisfying compatibility with achievement of high resolution of the primary beam.

In the absence of the deflection in y direction effected by means of the quaternary pole ExB deflector, for the sake of obtaining efficiently an image signal representing secondary electrons having ascended through the reflecting plate 13 by means of the upper detector 14, the pass aperture 215 in reflecting plate 15 needs to be as small as possible to reduce upward passage of the secondary electrons through the pass aperture 215. But, to enable the primary beam from above to pass, a pass aperture of about 1 mmΦ at the least is required and the loss of secondary electrons coming from below cannot be avoided. In addition, when the primary electron beam is deflected above the deflecting plate with the aim of applying tilting and alignment to the beam, the beam will impinge upon the reflecting plate 15 from above if the beam pass aperture 215 in the reflecting plate 15 is too small to pass the beam and the control range of beam is limited to a minimum.

To the contrary, since in the present embodiment the loss at the pass aperture can be eliminated by deflecting secondary electrons in the y direction, the beam pass aperture 215 in reflecting plate 15 can be sized more largely than that in other embodiments. As a result, even when the primary electron beam is desired to be deflected above the reflecting plate 15, the primary beam can be passed downwards without impinging on the reflecting plate 15 and the adjustment range and control capability of the electron optics can be improved to advantage.

Embodiment 4

Figure 10:
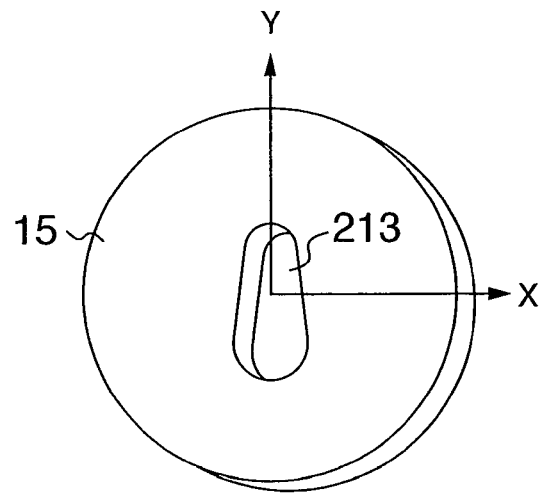
FIG. 10 is a bottom view of a reflecting plate shape according to a fourth embodiment.

As a fourth embodiment, an apparatus having an aperture 213 in the reflecting plate 13 shaped as shown in FIG. 10 was fabricated. The aperture in the reflecting plate is shaped to have its width changing in y direction. By deflecting secondary elections in the y direction through the use of this reflecting plate, components of secondary electrons impinging upon the reflecting plates 13 and 15 can be changed to permit a desired contrast to be obtained. More particularly, when the spreading radius of secondary electrons at the height of reflecting plate 13 is rse and secondary electrons spread to above the radius rse 1 (rse>rse 1) are desired to be detected at the reflecting plate 13, the secondary electrons are deflected to a position in the y direction at which an aperture diameter equaling rse 1 on the reflecting plate is defined. In case the radius of secondary electrons desired to be acquired changes, the amount of secondary electrons impinging on the reflecting plate can be adjusted by deflecting the secondary electrons in the y direction. This ensures that even when the electron optics condition such as boosting voltage for accelerating secondary electrons changes, the secondary electrons can be separated into desired components and detected at the reflecting plates 13 and 15 without being affected by the electron optics condition. Accordingly, the electron beam can be irradiated under a desired accelerating voltage condition in accordance with a specimen and the condition of electron beam landing on the specimen can be chosen under a more preferable condition.

Embodiment 5

Figure 11:
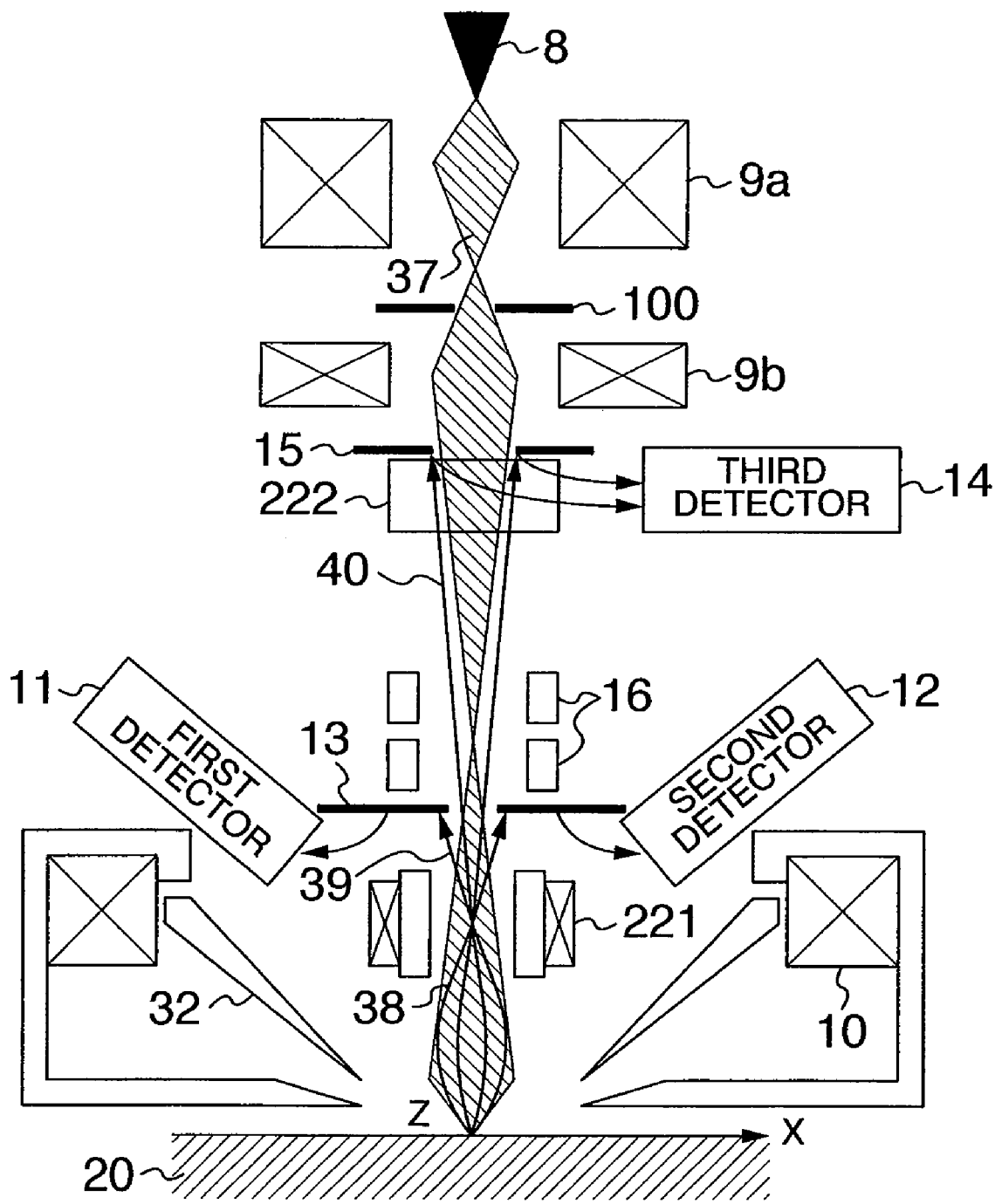
FIG. 11 is a schematic diagram showing the principal part of an example of electron optics according to a fifth embodiment.

A fifth embodiment will be described with reference to FIG. 11. In the present embodiment, the scan deflector 16 disposed more closely to the specimen than the reflecting plate 13 for shadow image formation and detectors 11 and 12 in the first embodiment is disposed on the electron gun side. Excepting the above structural difference, the present embodiment is identical to the first embodiment of FIG. 4. With this construction, the distance between the reflecting plate 13 and the specimen surface can be decreased and the axial shift of signal electrons at the reflecting plate 13 can be reduced relatively. Accordingly, the amount of deflection by the ExB 221 for alignment can be reduced and the influence of aberration on the primary beam can also be reduced. Further, since the reflecting plate 13 for shadow image formation and detectors 11 and 12 are closer to the specimen surface than the scan deflector 16, deflection of signal electrons by the scan deflector 16 does not affect the shadow image and more uniform shadow images can be obtained. It is to be noted that in the present embodiment of FIG. 11, an additional ExB deflector 222 for attracting signal electrons to the detector 14 is provided. With this construction, signal electrons from the reflecting plate 15 can be detected efficiently without having the influence of deflection upon the primary beam.

Embodiment 6

Figure 12:
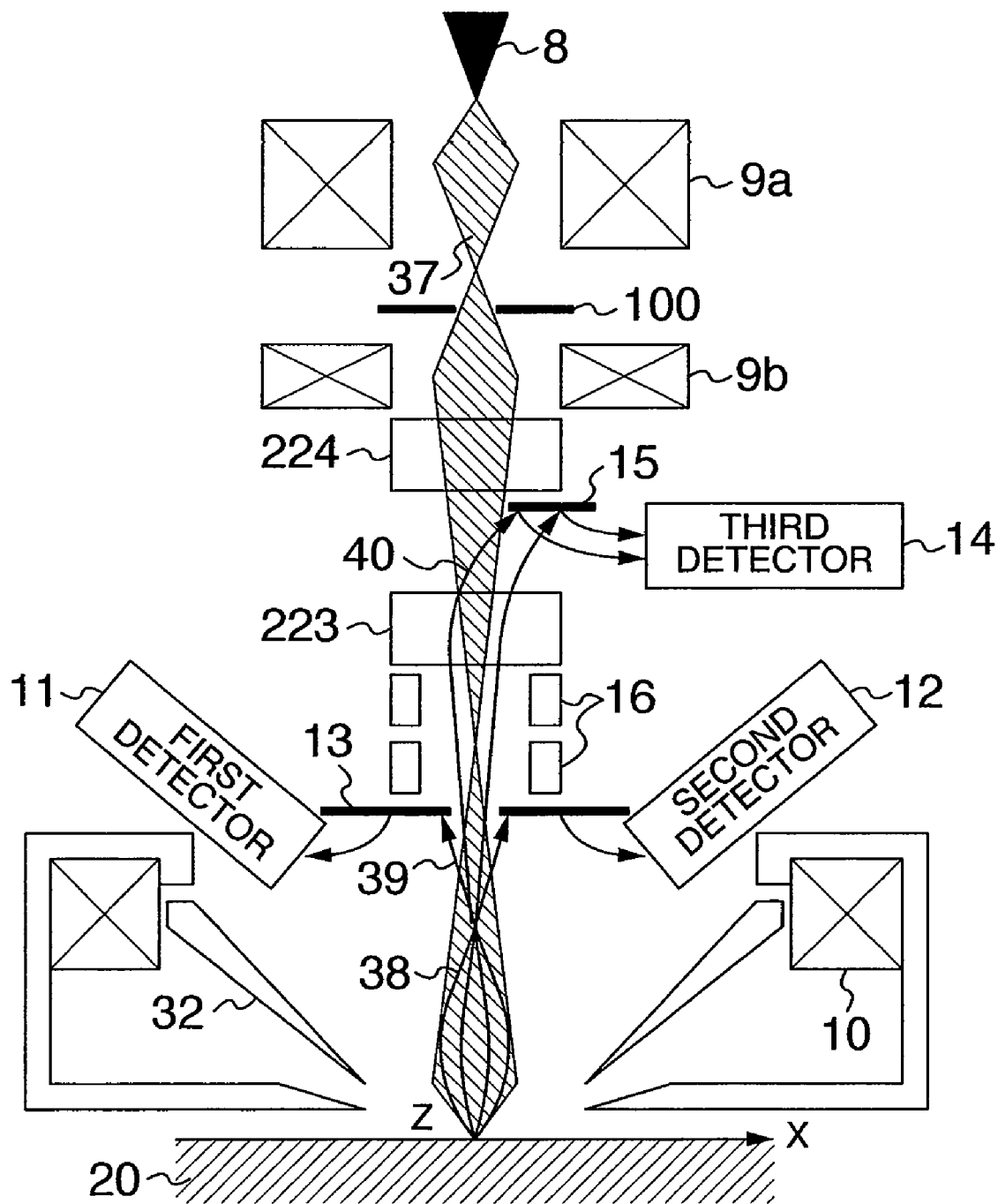
FIG. 12 is a schematic diagram showing the principal part of an example of electron optics according to a sixth embodiment.

A sixth embodiment will be described with reference to FIG. 12. In the present embodiment, with the aim of preventing an image signal to be picked up by the detector 14 from being affected by the loss due to the aperture in reflecting plate 15, an ExB deflector 223 is disposed more closely to the specimen than the reflecting plate 15 to thereby deflect signal electrons to the outside of optical axis. The ExB deflector 223 is interposed between the reflecting plates 13 and 15 to keep signal electrons from being affected by deflection at the reflecting plate 13. In the present embodiment, since the reflecting plate 13 is disposed more closely to the specimen surface than the scan deflector 16 and the axial shift of signal electrons at the reflecting plate 13 does not affect the shadow image greatly, the ExB deflector 221 for alignment is not provided.

The signal electrons have, as shown in FIG. 3, a component emitting from the specimen surface at an energy range of from 1 eV to several of 10 eV (hereinafter referred to as a low energy component) and a component emitting at a level of energy substantially equal to that of the primary beam (hereinafter referred to as a high energy component). The high energy component is a component of so-called backscattering electrons. Signal electrons passing upwards without impinging upon the reflecting plate 13 mainly include the low energy component but even electrons corresponding to the low energy component pass through the retarding electric field nearby the specimen surface so as to be accelerated to an energy level of about 1 KeV corresponding to the retarding potential. Accordingly, in order to deflect the signal electrons at about 1 KeV or more to make them clear of the optical axis, the ExB deflector needs to be so conditioned operationally as to apply an electric field corresponding to a high voltage of, for example, 10V or more and a magnetic field commensurate therewith. Therefore, another stage of E×B deflector 224 is arranged between the reflecting plate 15 and the electron gun to generate an electromagnetic field of polarity inverse to that of the electromagnetic field by the E×B deflector 223, thereby ensuring that chromatic aberration of the primary beam caused by the E×B deflector 223 can be canceled by the E×B deflector 224. With the above construction, a signal can be obtained with high efficiency by causing the signal electrons for formation of a shadow image to impinge upon the reflecting plate 13 so as to obtain signals at the detectors 11 and 12 and resultant shadow images and also other signal secondary electrons can be obtained by deflecting the signal electrons to the outside of the optical axis while enabling them to deviate from the aperture in the reflecting plate 15. Balancing between the shadow image signal obtained at the reflecting plate 13 and the signal obtained at the reflecting plate 15 is determined by an electric field distribution superimposed on the objective lens 10 and the diameter of aperture in the reflecting plate 13 as well. Accordingly, under the operational condition of the electron immersion lens for achieving high resolution, the reflecting plate 13 is so designed as to have an aperture diameter which permits separation at desired threshold values $E_t$ and $\theta_t$ of energy $E$ and angle $\theta$ at the time of upward emission of the signal electrons from the specimen.

Embodiment 7

Figure 13:
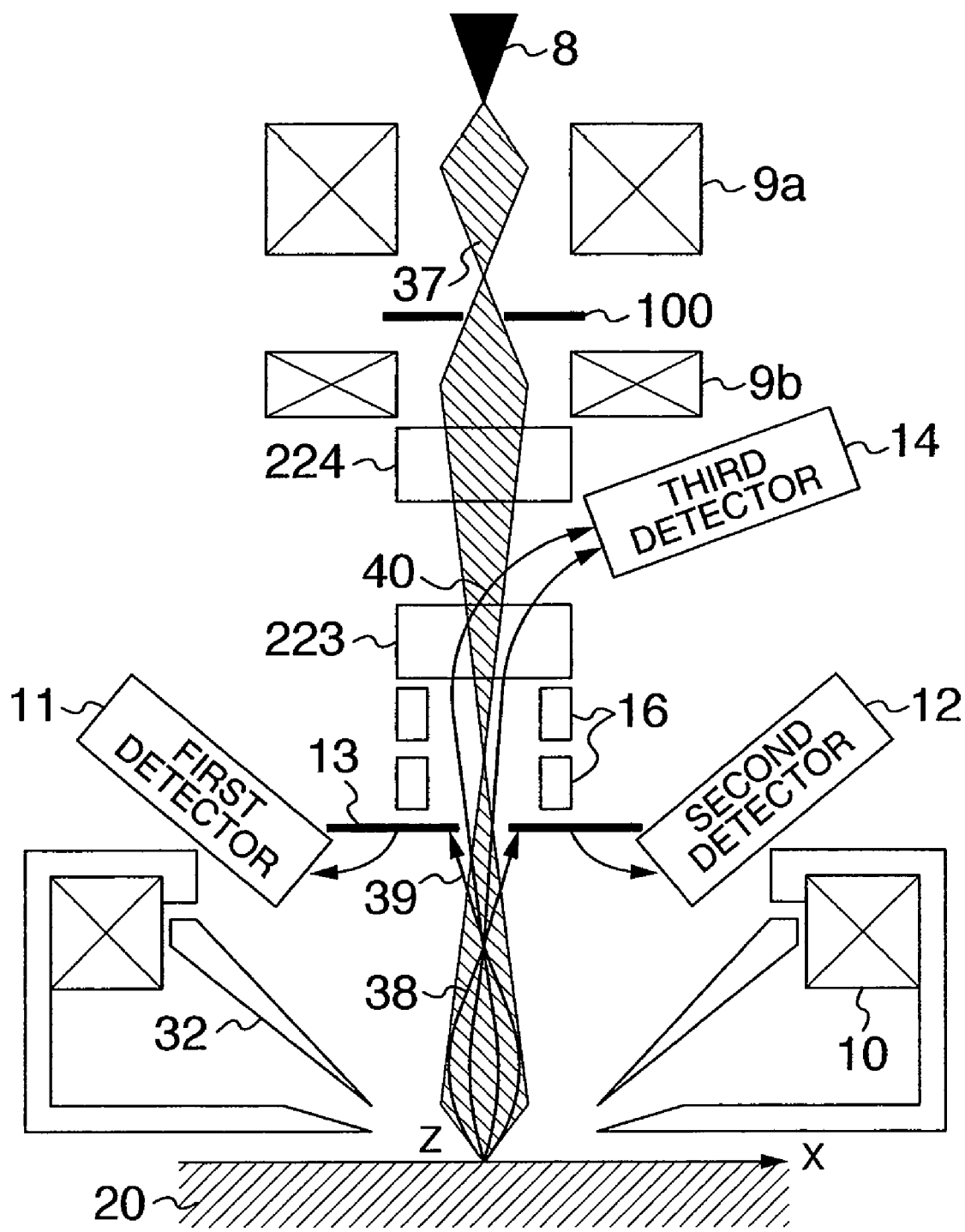
FIG. 13 is a schematic diagram showing the principal part of an example of electron optics according to a seventh embodiment.

A seventh embodiment is carried out in which the detector 14 and reflecting plate 15 in the sixth embodiment (FIG. 12) are replaced with a detector 14 which is so arranged as to directly detect signal electrons. The present embodiment is illustrated in FIG. 13. With this construction, the loss of signal electrons in course of attracting electrons from the reflecting plate or the intermixing of noise can be avoided to permit acquisition of high S/N signals.

Figure 14:
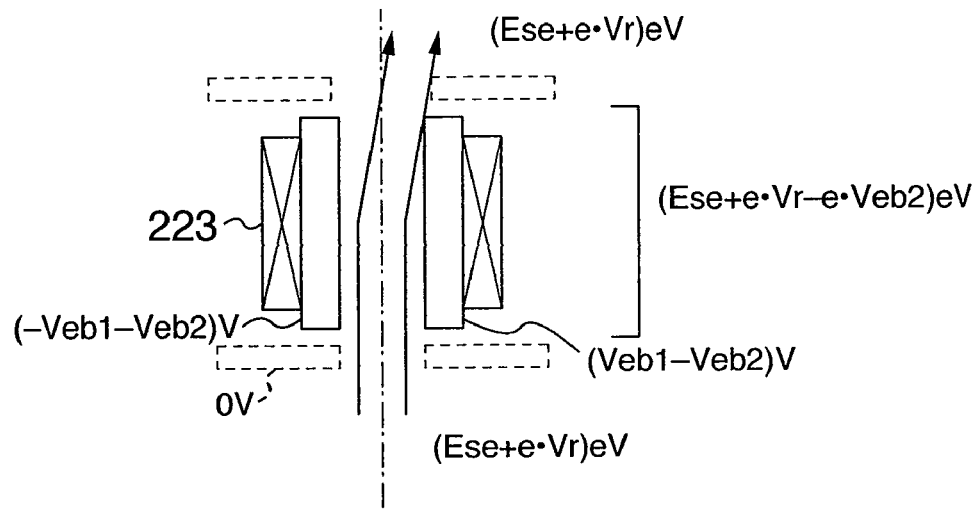
FIG. 14 is a diagram showing the operation state of an E×B deflector in the seventh embodiment.

Structurally, the E×B deflector 223 in the present embodiment may be mounted with a power supply as shown in FIG. 14 for further superimposing decelerating potential in order that signal electrons can be decelerated to a desired energy level. If, in the absence of the deceleration, the electrode of the E×B deflector is applied with a potential level of ±Veb1, a potential level of (−Veb2) is superimposed on the electrode to thereby apply a potential level of (±Veb1−Veb2). In this manner, only during passage through the E×B deflector 223, energy of secondary electrons is reduced for deceleration. For the purpose of generating the decelerating potential distribution in the vicinity of only the E×B deflector, electrodes at ground potential may be mounted to upper and lower ends of the E×B deflector.

In this case, even with the operating electromagnetic field of E×B deflector decreased, energy of signal electrons is reduced for deceleration and the signal electrons can be deflected to a desired position at the reflecting plate 15. Through this, the influence of chromatic aberration caused by the E×B deflector can further be decreased.

Structurally, the detector 14 may be formed of a plurality of detector sections to ensure that separating and detection can be accomplished in accordance with a slight difference in deflection angle of signal electrons in the E×B deflector 223. Signal electrons having passed upwards without impinging upon the reflecting plate 15 include, though by a slight amount, signal electrons of a high energy component emitting vertically from the specimen. By separating the high energy component, a substance contrast signal, that is, a pure, so-called secondary electron signal, can be acquired.

In the present embodiment, an E×B deflector 221 for alignment can be interposed between the reflecting plate 13 and the specimen surface.

Embodiment 8

Figure 15:
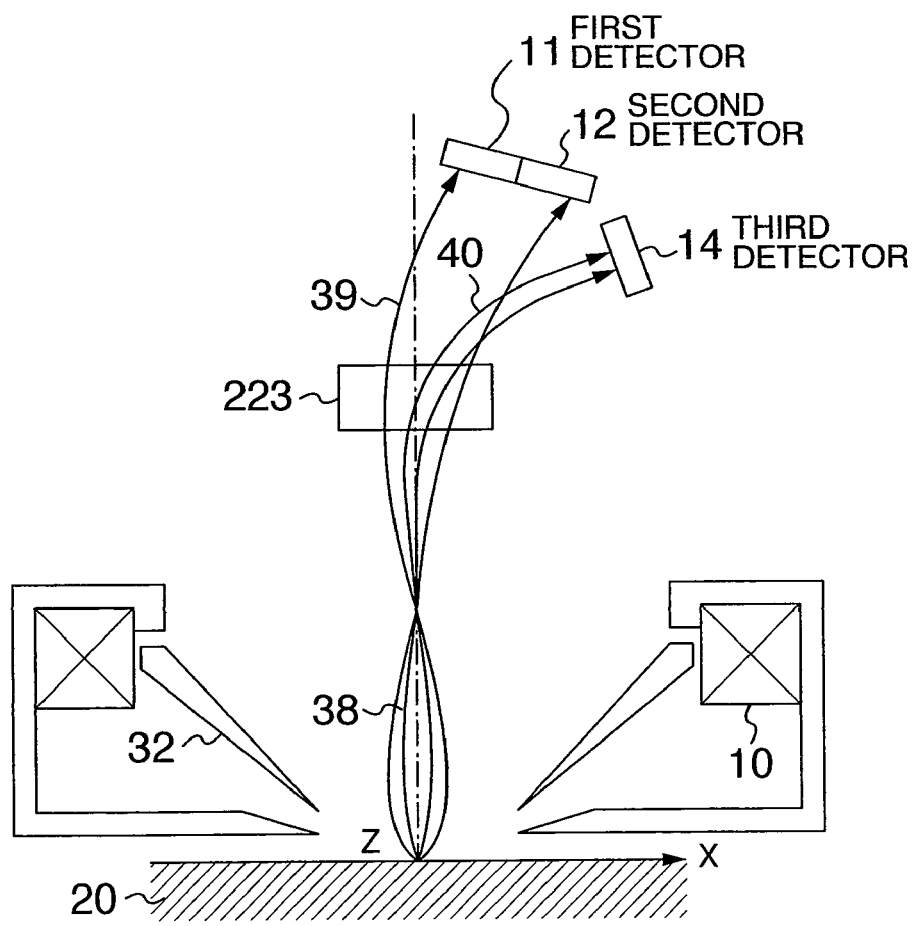
FIG. 15 is a schematic diagram showing the principal part of an example of electron optics according to an eighth embodiment.

An eighth embodiment will be described with reference to FIG. 15. In the present embodiment, the reflecting plate 13 is omitted, detectors 11 and 12 are arranged more closely to the electron gun than the E×B deflector 223 and detectors 11, 12 and 14 are all arranged to get clear of the optical axis. The remaining components are similar to those in the seventh embodiment of FIG. 13 and will not be described herein. In the E×B deflector 223, the signal electrons as a whole are deflected and at the same time, decelerating potential is applied to reduce the energy of the signal electrons for deceleration. In consequence, the angle of deflection by the E×B deflector 223 becomes irregular to a great extent depending on the energy of the signal electrons. By making the use of the difference in deflection angle, a high energy component of the signal electrons is acquired by means of the detectors 11 and 12 close to the optical axis and a lower energy component is acquired by means of the detector 14 remote from the optical axis, thus making it possible to sort signal electrons. Through this, with the drastically simplified construction, simultaneous acquisition of the shadow image and the substance contrast image can be assured highly efficiently and uniformly while maintaining the resolution.

Embodiment 9

Figure 16:
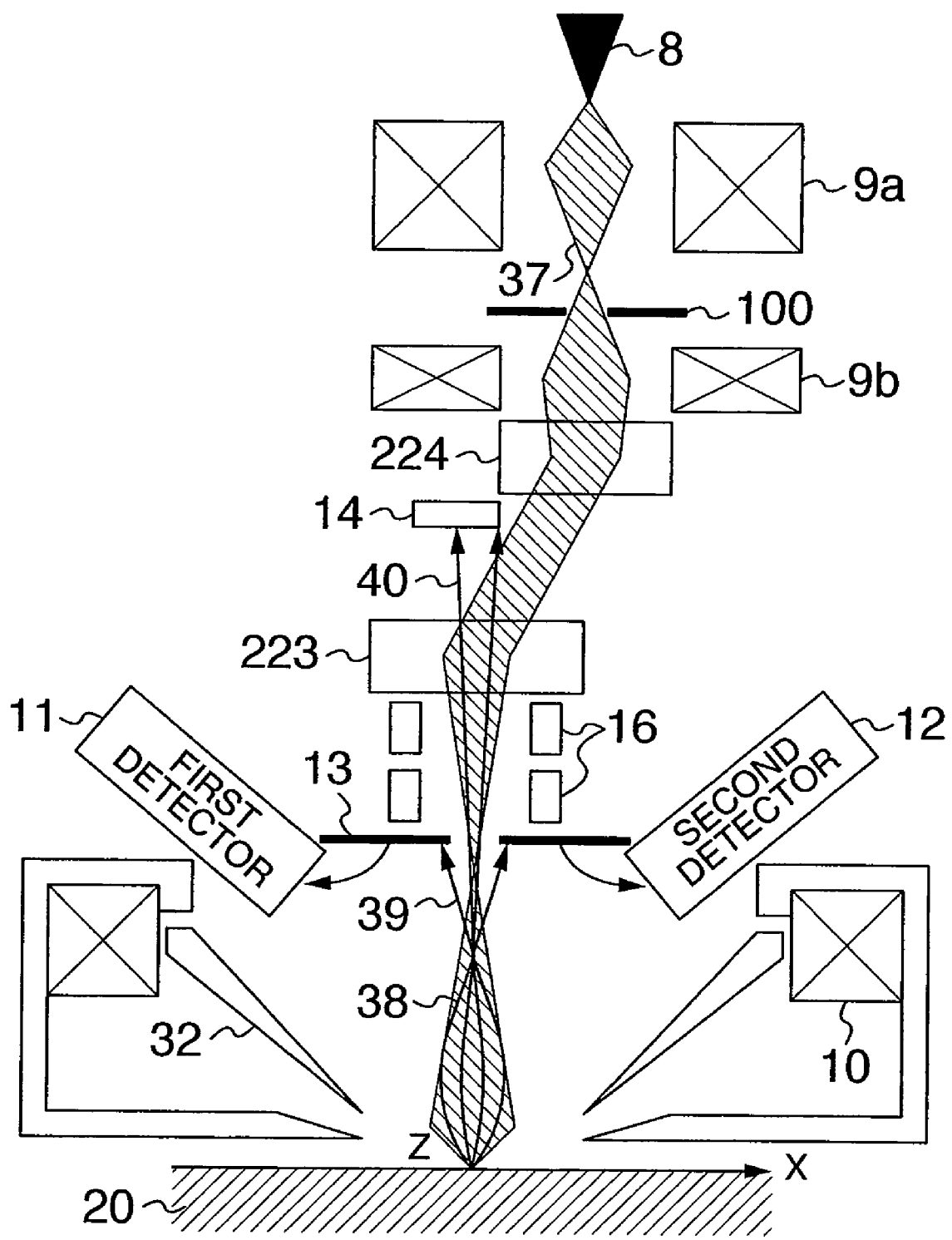
FIG. 16 is a schematic diagram showing the principal part of an example of electron optics according to a ninth embodiment.

Turning now to FIG. 16, a ninth embodiment will be described. According to the present embodiment, in the construction of the seventh embodiment, constituent parts ranging from the lower E×B deflector 223 to the specimen are arranged to have an axis different from the optical axis of electron gun 8 and the detector 14 is arranged to have an axis coincident with the optical axis of electron gun 8. The primary electron beam is sequentially deflected by means of the E×B deflectors 224 and 223 and on the other hand, secondary electrons generated from the specimen are hardly deflected by means of the E×B deflector 223. Even with this construction, because of the two stages of E×B deflector, the influence of aberration upon the primary electron beam can be reduced to some extent and a detection system can be constructed in which degradation in resolution can be lessened and the detection efficiency can be rendered high.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A review apparatus which acquires an image by detecting secondary electron or back scattering electron generated by irradiating an electron beam to a sample, the apparatus comprising:
   a beam source for generating a primary charged particle beam;
   a scan deflector for scanning the primary charged particle beam;
   a primary deflection unit for deflecting the primary charged particle beam;
   a secondary deflection unit for separating the secondary electron or the backscattering electron from the primary charged particle beam, wherein said secondary deflection unit is disposed between the beam source and the scan deflector;

a primary detector disposed between the primary deflection unit and the secondary deflection unit;

a plurality of secondary detectors disposed on a side of the sample near the primary deflector unit, the secondary deflector unit and the scan deflector; and an objective lens for focusing said primary charged particle beam on the sample.

2. The review apparatus according to claims 1, wherein the primary deflection unit and the secondary deflection unit are ExB deflectors.

3. The review apparatus according to claim 1, wherein the plurality of secondary detectors are formed by a disposition of detectors of axially symmetrical shape.

4. The review apparatus according to claim 1, wherein the primary deflection unit generates an electromagnetic field of polarity inverse to polarity of an electromagnetic field of the second deflection unit.

5. The review apparatus according to claim 1, wherein the plurality of secondary detectors are disposed in azimuth directions in which a center axis is the optical axis of the objective lens.

6. The review apparatus according to claim 5, wherein the azimuth directions are rotational directions around a normal line of the sample.

7. The review apparatus according to claim 1, wherein the primary detector is disposed on an extension line of the optical axis of the objective lens.

* * * * *